United States Patent
Song et al.

(10) Patent No.: US 10,512,670 B2
(45) Date of Patent: *Dec. 24, 2019

(54) PHARMACEUTICAL COMPOSITION FOR PREVENTING OR TREATING HAIR LOSS COMPRISING CHEMOKINE (C-X-C MOTIF) LIGAND 1 (CXCL1) PROTEIN OR CXCL1 PROTEIN AND MINOXIDIL AS ACTIVE INGREDIENT

(71) Applicant: SCM LIFESCIENCE CO., LTD., Incheon (KR)

(72) Inventors: Sun Uk Song, Incheon (KR); Jong Hyuk Sung, Seongnam-si (KR)

(73) Assignee: SCM LIFESCIENCE CO., LTD., Incheon (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/014,812

(22) Filed: Jun. 21, 2018

(65) Prior Publication Data

US 2018/0289772 A1 Oct. 11, 2018

Related U.S. Application Data

(63) Continuation-in-part of application No. 15/317,895, filed as application No. PCT/KR2016/014234 on Dec. 6, 2016.

(30) Foreign Application Priority Data

Aug. 8, 2016 (KR) .................. 10-2016-0100966

(51) Int. Cl.
| | |
|---|---|
| A61K 38/00 | (2006.01) |
| A61K 38/19 | (2006.01) |
| A61K 31/506 | (2006.01) |
| A23L 33/17 | (2016.01) |
| A23L 2/66 | (2006.01) |
| A61P 17/14 | (2006.01) |

(52) U.S. Cl.
CPC .............. *A61K 38/19* (2013.01); *A23L 2/66* (2013.01); *A23L 33/17* (2016.08); *A61K 31/506* (2013.01); *A61P 17/14* (2018.01); *A23V 2002/00* (2013.01)

(58) Field of Classification Search
None
See application file for complete search history.

(56) References Cited

U.S. PATENT DOCUMENTS

2008/0287349 A1 11/2008 Peterson et al.
2015/0290104 A1 10/2015 Woodward et al.

FOREIGN PATENT DOCUMENTS

| KR | 10-2010-0032099 A | 3/2010 |
| WO | 2012/061537 A2 | 5/2012 |
| WO | WO 2012/061537 A2 | 5/2012 |

OTHER PUBLICATIONS

Zainodini, Iran.J.Immunol., vol. 10 No. 1 Mar. 2013, 40-46 (Year: 2013).*
Kim et al., "Polymorphisms in the promoter regions of the CXCL1 and CXCL2 genes contribute to increased risk of alopecia areata in the Korean population," Genetics and Molecular Research, vol. 14, No. 3, pp. 9667-9674, 2015.
Zainodini et al., "Differential Expression of CXCL1, CXCL9 CXCL10 and CXCL12 Chemokines in Alopecia Areata," Iran. J. Immunol., vol. 10, No. 1, pp. 40-46, Mar. 2013.
Li et al., "Laser Capture Microdissection Reveals Transcriptional Abnormalities in Alopecia Areata before, during, and after Active Hair Loss," Journal of Investigative Dermatology, vol. 136, pp. 715-718, 2016.
Subramanya et al., "Transcriptional profiling in alopecia areata defines immune and cell cycle control related genes within disease-specific signatures," Genomics, vol. 96, pp. 146-153, 2010.
Li et al., "Laser Capture Microdissection Reveals Transriptional Abnormalities in Alopecia Areata before, during, and after Active Hair Loss," *Journal of Investigative Dermatology*, vol. 136, pp. 715-718, 2016.

* cited by examiner

*Primary Examiner* — Satyanarayana R Gudibande
(74) *Attorney, Agent, or Firm* — Joseph Hyosuk Kim; Nixon & Vanderhye P.C.

(57) ABSTRACT

Provided is a composition for preventing, treating or improving hair loss and promoting hair generation and hair growth, comprising a CXCL1 protein as an active ingredient. Further, provided is a composition for preventing, treating or improving hair loss and promoting hair generation and hair growth, comprising a CXCL1 protein and minoxidil as an active ingredient. The CXCL1 protein according to the present disclosure has no side effects at the time of treating hair loss and an excellent hair generation effect even in a short time and thus can be used as pharmaceutical products and usefully used as quasi-drugs, cosmetics and health functional foods.

6 Claims, 4 Drawing Sheets

Specification includes a Sequence Listing.

[FIG. 1]
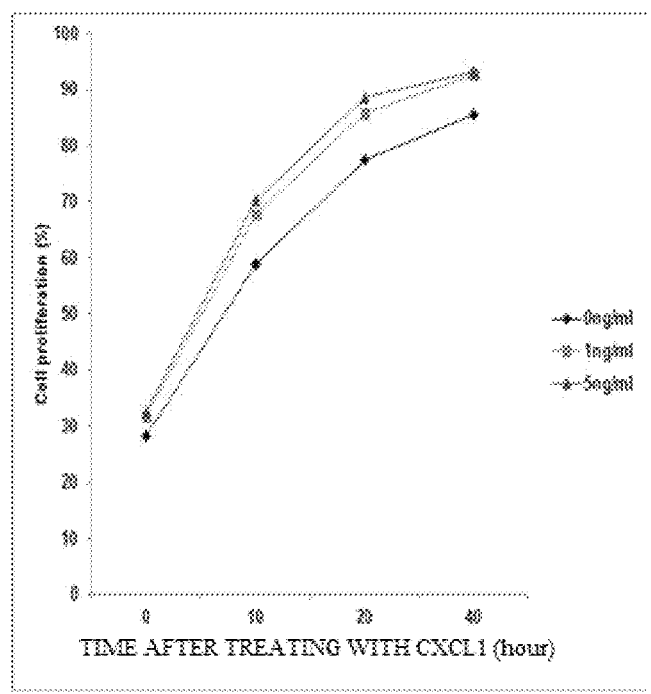

[FIG. 2]
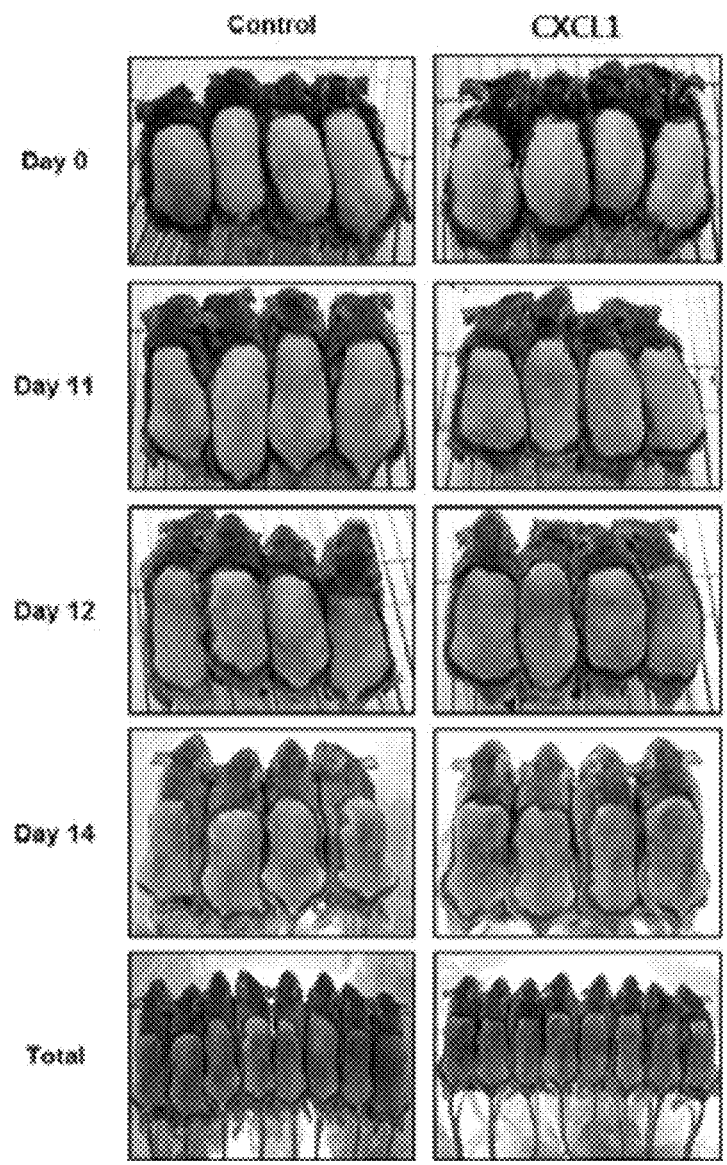

[FIG. 3]
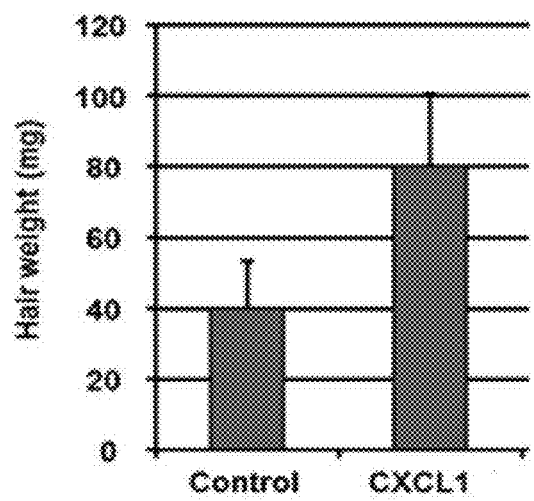
[FIG. 4]
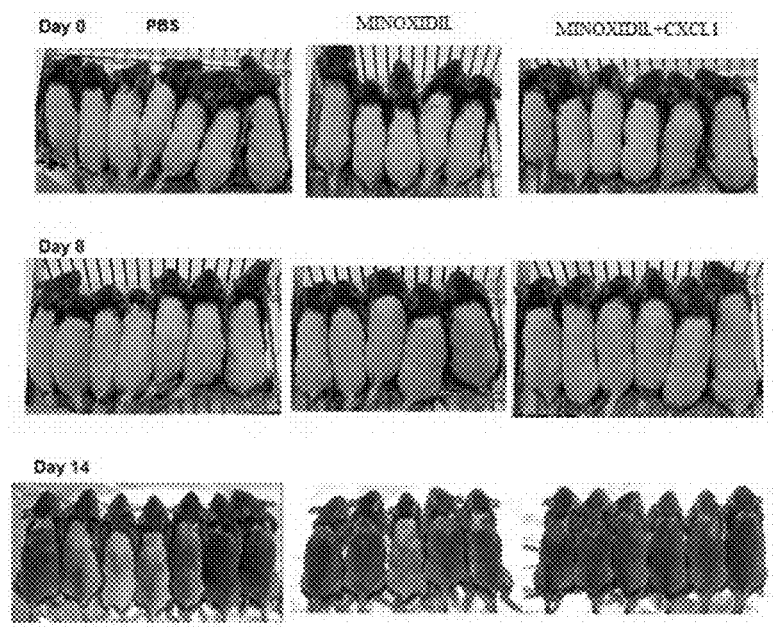

[FIG. 5]
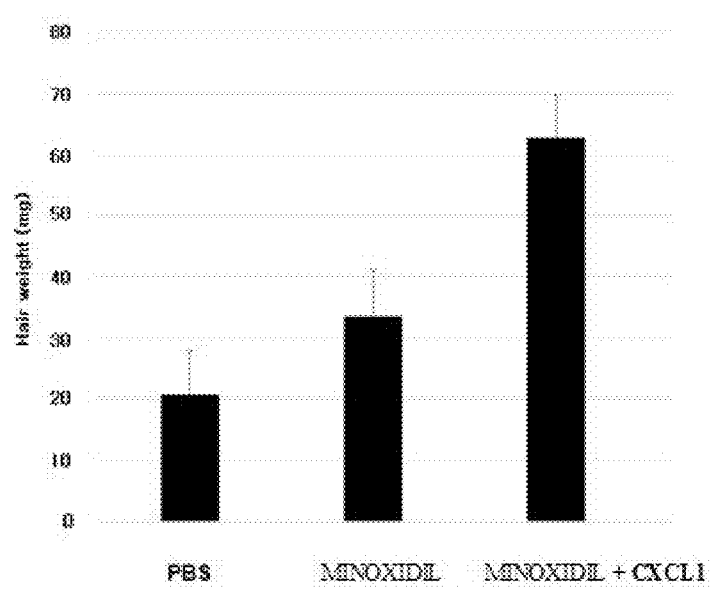

PHARMACEUTICAL COMPOSITION FOR PREVENTING OR TREATING HAIR LOSS COMPRISING CHEMOKINE (C-X-C MOTIF) LIGAND 1 (CXCL1) PROTEIN OR CXCL1 PROTEIN AND MINOXIDIL AS ACTIVE INGREDIENT

TECHNICAL FIELD

The present application discloses a composition for preventing, treating or improving hair loss, which comprises a CXCL1 (chemokine (C-X-C motif) ligand 1) protein, or a CXCL 1 protein and minoxidil as an active ingredient, and a composition for promoting hair generation or hair growth.

BACKGROUND

Hair loss means a state without hair in a region where hair normally exists, and means that generally, the grown hair (coarse black hair) of the scalp is lost. The grown hair is lost unlike soft hair having no color and a thin thickness to cause a cosmetic problem. In the case of Koreans with lower hair density than Westerners, there are between 50,000 and 70,000 hair and about 50 to 70 hair are normally lost per day. Accordingly, if the number of hair lost when you sleep or clean your hair exceeds 100, hair loss may be ongoing.

The causes of hair loss are diverse, and genetic causes and androgen as a male hormone are considered to be important factors in the development of baldness. It is presumed that the female pattern hair loss occurs in the same way as male pattern hair loss, but there is a difference in clinical appearance. Alopecia areata is considered to be an autoimmune disease. Telogen effluvium is temporary hair loss caused by severe physical and mental stresses such as endocrine diseases, malnutrition, drug use, birth, fever, and surgery and caused by a part of the hair which does not fill the growth period and falls into the dormant state.

Further, among these symptoms of hair loss, male hair becomes thin and hair loss is in progression of hair from a person who has a family history of baldness from the twenties or thirties. The border between forehead and head is pushed backward, and the forehead spreads in M-shape on both sides of the head, and hair loss gradually progresses to the head parietal region. The female hair loss is characterized by thinning the hair in the center of the head while the hair line on the forehead is maintained as compared with the male hair loss. Also, it is rare for female hair loss to result in complete baldness because the degree of hair loss is weak. Further, alopecia areata is characteristic in the appearance of circular or oval depilatories with various sizes (hair is lost and looks like dots). Alopecia areata occurs mainly in the head, and rarely, occurs in beard, eyebrows and eyelashes, and a large depilatory is formed while enlarging the symptom area. If the entire hair falls off, it will be classified into all-hair alopecia (frontal hair alopecia) and whole-hair alopecia if the whole hair is lost. In addition, telogen effluvium is caused by entirely reducing the hair from 2 to 4 months after the cause stimulus occurs, and when the cause stimulus is removed, hair loss is reduced as the dormant hair returns to normal over several months.

On the other hand, in the case of male or female hair loss, as methods for treating the hair loss in the related art, drugs of applying minoxidil and the like, drugs of eating finasteride and the like, and hair transplantation have been used. In addition, for treating alopecia areata, topical steroids or systemic steroids, immunotherapy, and the like have been used. In telogen effluvium, it is important to identify and treat the cause because hair is recovered when the cause is removed. However, in the case of treating hair loss by the conventional method, there is a problem of side effects by depending on a drug therapy or a steroid preparation, and because the speed of treatment is not fast, there is a problem in long-term. In addition, in treatment with drugs or hair transplantation, there is a problem that the treatment cost is greatly increased. Minoxidil and Finasteride are representative drugs used to promote hair growth. Minoxidil of Upjohn Corporation in the US can cause side effects such as edema, arrhythmia and hairiness in long-term application, and the effect of minoxidil is most effective from 6 months to 1 year after use, and thereafter, it is known that the effect is slowly reduced. In addition, finasteride developed by Merck Corporation is known as a material which inhibits the activity of 5-α-reductase as an enzyme that acts on the male hormone testosterone metabolism in hair follicles, but it is reported that sexual dysfunction, depression and suicidal impulses are increased. In addition, since the possibility of birth defects is increased, it is not applicable to women in fertility or pregnant women. In addition, it is known that when the application of both drugs is discontinued, hair loss again occurs. In addition, there is a valproic acid, but it is known that the children's cognitive development ability is greatly reduced when it is taken during pregnancy. Thus, in various conventional types of hair generation agents, a method of helping hair growth for the purpose of accelerating blood circulation and nourishment of hair follicles has generally been attempted, but the toxicity and side effects are also severe and the effect thereof is insufficient at present.

DISCLOSURE

Technical Problem

Therefore, the inventors made efforts to develop materials capable of preventing hair loss and promoting hair generation without side effects and thus verified that the CXCL1 protein in the body had an effect of promoting hair growth and completed the present disclosure.

The present disclosure has been made in an effort to provide a pharmaceutical composition for preventing or treating hair loss comprising a chemokine (C-X-C motif) ligand 1 (CXCL1) protein; or a CXCL1 protein and minoxidil as an active ingredient.

The present disclosure has been also made in an effort to provide a quasi-drug composition, a cosmetic composition and a food composition for preventing or improving hair loss comprising a CXCL1 (chemokine (C-X-C motif) ligand 1) protein; or a CXCL1 protein and minoxidil as an active ingredient.

The present disclosure has been also made in an effort to provide a pharmaceutical composition, a quasi-drug composition, a cosmetic composition and a food composition for promoting or stimulating hair generation or hair growth comprising a CXCL1(chemokine (C-X-C motif) ligand 1) protein; or a CXCL1 protein and minoxidil as an active ingredient.

The present disclosure has been also made in an effort to provide a complex formulation for preventing or treating hair loss comprising a CXCL1(chemokine (C-X-C motif) ligand 1) protein; or a CXCL1 protein and minoxidil.

Technical Solution

An exemplary embodiment of the present disclosure provides a pharmaceutical composition for preventing or treating hair loss comprising a CXCL1 (chemokine (C-X-C motif) ligand 1) protein; or a CXCL1 protein and minoxidil as an active ingredient.

Further, another exemplary embodiment of the present disclosure provides a quasi-drug composition for preventing or improving hair loss comprising a CXCL1 (chemokine (C-X-C motif) ligand 1) protein; or a CXCL1 protein and minoxidil as an active ingredient.

Further, yet another exemplary embodiment of the present disclosure provides a cosmetic composition for preventing or improving hair loss comprising a CXCL1 (chemokine (C-X-C motif) ligand 1) protein; or a CXCL1 protein and minoxidil as an active ingredient.

Further, still another exemplary embodiment of the present disclosure provides a food composition for preventing or improving hair loss comprising a CXCL1(chemokine (C-X-C motif) ligand 1) protein; or a CXCL1 protein and minoxidil as an active ingredient.

Further, still yet another exemplary embodiment of the present disclosure provides a pharmaceutical composition for promoting hair generation or hair growth comprising a CXCL1 (chemokine (C-X-C motif) ligand 1) protein; or a CXCL1 protein and minoxidil as an active ingredient.

Further, still yet another exemplary embodiment of the present disclosure provides a quasi-drug composition for promoting hair generation or hair growth comprising a CXCL1 (chemokine (C-X-C motif) ligand 1) protein; or a CXCL1 protein and minoxidil as an active ingredient.

Further, still yet another exemplary embodiment of the present disclosure provides a cosmetic composition for promoting hair generation or hair growth comprising a CXCL1 (chemokine (C-X-C motif) ligand 1) protein; or a CXCL1 protein and minoxidil as an active ingredient.

Further, still yet another exemplary embodiment of the present disclosure provides a food composition for promoting hair generation or hair growth comprising a CXCL1 (chemokine (C-X-C motif) ligand 1) protein; or a CXCL1 protein and minoxidil as an active ingredient.

Further, still yet another exemplary embodiment of the present disclosure provides a complex formulation for preventing or treating hair loss comprising a CXCL1 (chemokine (C-X-C motif) ligand 1) protein and minoxidil.

Advantageous Effects

According to the exemplary embodiment of the present disclosure, the composition for preventing hair loss or promoting hair generation comprising the CXCL1 protein, or the CXCL1 protein and the minoxidil as an active ingredient according to the present disclosure has no side effects at the time of treating hair loss and an excellent hair generation effect even in a short time and thus can be used as pharmaceutical products and usefully used as quasi-drugs, cosmetics and health functional foods.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a diagram illustrating a result of measuring cell proliferation for 40 hrs after a CXCL1 protein is treated to DPC.

FIG. 2 is a diagram illustrating a photograph of the back of a mouse after 15 days after hair of the back of a C3H/HeN mouse is removed using a hair removal agent and the CXCL1 protein is subcutaneously injected.

FIG. 3 is a diagram illustrating a result of measuring an increased hair weight (mg) of the mouse after 15 days after hair of the back of a C3H/HeN mouse is removed using a hair removal agent and the CXCL1 protein is subcutaneously injected.

FIG. 4 is a diagram illustrating a photograph of the back of a mouse after 14 days after hair of the back of a C3H/HeN mouse is removed using a hair removal agent and PBS, minoxidil, and the minoxidil and the CXCL1 protein are applied.

FIG. 5 is a diagram illustrating a result of measuring an increased hair weight (mg) of the mouse after 14 days after hair of the back of a C3H/HeN mouse is removed using a hair removal agent and PBS, minoxidil, and the minoxidil and the CXCL1 protein are applied.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure will be described in detail.

The present disclosure provides a pharmaceutical composition for preventing or treating hair loss and a pharmaceutical composition for promoting hair generation or hair growth, comprising a CXCL1 protein as an active ingredient.

Chemokine (C-X-C motif) ligand 1 (CXCL1) is a kind of chemokine belonging to a CXC family Chemokine is a basic heparin-binding low-molecular protein for leukocytes migration and activation. Four cysteine residues exist in the chemokine molecule and first two cysteine residues in the molecule are classified into four subspecies of CXC(CXCL), CC(CCL), CX3C(CX3CL), and C(XCL) in the existence type and 40 species or more are identified at present. The CXCL1 protein is secreted by human melanoma cells and has a mitosis promoting property and is involved the cause of melanoma. The CXCL1 protein is expressed in macrophages, neutrophils and epithelial cells and has a neutrophil activation function. The CXCL1 protein exhibits the effect by signaling through a chemokine receptor CXCR2 and is involved in inflammatory response, wound healing, and tumorigenesis.

The CXCL1 protein may be configured by all or some peptides having an effect of preventing or treating hair loss and promoting hair generation or hair growth, and may be preferably configured by an amino acid sequence of SEQ ID NO:1, and functional equivalents and variants of the protein thereof.

The functional equivalent of the protein includes proteins and polypeptides without entirely changing the activity of the protein molecule and proteins having functionally the same action are included in the scope of the present disclosure. The variant means for example, deletion, substitution, or addition of one or several amino acids in the amino acid sequence and has identify of 95% or more, preferably 98% or more, and more preferably 99% or more with the amino acid sequence. Herein, the "identity" means a ratio (%) of the number of the same amino acid residues in the other amino acid sequence to all amino acid residues of one amino acid sequence including the number of gaps, when a gap is introduced to two amino acid sequences or the two amino acid sequences are aligned to have the highest coherency without introducing the gap. Further, "several" means an integer of 2 to 10, for example, 2 to 7, 2 to 5, 2 to 4, and 2 to 3. Particular examples of natural variants may include variants, splice variants, or the like based on polymorphisms such as SNP (monospecific polymorphism). The substitution is preferably conservative amino acid substitution. The conservative amino acid substitution may have a substantially equal structure or property to human CXCL1 having the amino acid sequence. As the conservative amino acid, nonpolar amino acids (glycine, alanine, phenylalanine, valine, leucine, isoleucine, methionine, proline and tryptophan), polar amino acids (amino acids other than nonpolar amino acids), charged amino acids (acidic amino acids (aspartic acid and glutamic acid) and basic amino acids (arginine, histidine, and lysine), non-charged amino acids (amino acids other than charged amino acids), aromatic amino acids (phenylalanine, tryptophan, and tyrosine), branched amino acids (leucine, isoleucine, and valine), aliphatic amino acids (glycine, alanine, leucine, isoleucine, and valine), and the like are known. Further, proteins with increased structural stability to heat, pH, or the like of the protein or increased protein activity by mutation or modification of the amino acid sequence.

A gene coding the CXCL1 protein may be constituted by a base sequence of SEQ ID NO:2, and the variants which may have functionally the same function as the nucleotide are included in the scope of the present disclosure.

The variants which may have functionally the same function have sequence homology of at least 70% or more, preferably 80% or more, more preferably 90% or more, and much more preferably 95% or more with the base sequence represented by SEQ ID NO:2 as a result of addition, substitution or deletion of the base and mean a base sequence which may code a protein having substantially the same physiological activity as the protein coded by the base sequence represented by SEQ ID NO:2. For example, some base sequences are modified by deletion, substitution or insertion, but include variants which may have functionally the same action as a nucleic acid molecule coding the CXCL1 protein.

The term "hair loss" used in this specification may belong to cases where the number of hair is smaller than the general number beyond a normal hair level without a particular limitation, and preferably, any one or more selected from the group consisting of male pattern hair loss, female pattern hair loss, round hair loss and resting hair loss may correspond to hair loss which is treated or prevented by the composition according to the present disclosure. Further, the composition according to the present disclosure has an excellent effect of preventing hair loss before hair loss starts.

The term "hair generation" used in this specification means that hair is generated and "hair growth" means that hair grows. An effect of the composition according to the present disclosure also includes an effect of promoting hair generation or hair growth.

The term "preventing" used in this specification means all activities which suppress or delay hair loss by administering the composition of the present disclosure and the "treating" means all activities which improve or beneficially change symptoms associated with hair loss by the composition of the present disclosure.

The pharmaceutical composition of the present disclosure may further include a carrier, an excipient, and a diluent which are properly and generally used in preparation of the pharmaceutical composition. Further, the pharmaceutical composition of the present disclosure may be formulated and used in the form of an oral formulation such as a powder, a granule, a tablet, a capsule, a suspension, an emulsion, syrup, or an aerosol, an external preparation, a suppository, or a sterile injection solution according to a general method. It is preferred that a suitable formulation which is known in the art uses a formulation disclosed in the document.

The carrier, the excipient, and the diluent which may be included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, or mineral oil.

When the pharmaceutical composition according to the present disclosure is formulated, the formulation may be prepared by using a diluent or an excipient, such as a filler, an extender, a binder, a wetting agent, a disintegrating agent, and a surfactant which are generally used. A solid formulation for oral administration may include a tablet, a pill, a powder, a granule, a capsule, or the like, and the solid formulation may be prepared by mixing at least one excipient, for example, starch, calcium carbonate, sucrose, lactose, gelatin, and the like with the active ingredient. Further, lubricants such as magnesium stearate and talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin which are commonly used simple diluents. A formulation for parenteral administration may include a sterile aqueous solution, a non-aqueous solution, a suspension, an emulsion, and a lyophilizing agent, and a suppository. As the non-aqueous solution and the suspension, propylene glycol, polyethylene glycol, vegetable oils such as olive oil, injectable ester such as ethyl oleate, and the like may be used. As a matter of the suppository, witepsol, macrogol, Tween® 61, cacao butter, laurin, glycerogelatin, and the like may be used.

The composition of the present disclosure may be administered with a pharmaceutically effective dose.

In the present disclosure, the term "pharmaceutically effective dose" means an amount which is sufficient to treat the condition at a reasonable benefit/risk ratio applicable to medical treatment, and an effective dose level may be determined according to elements including a kind of disease of the patient, the severity, age of the patient, sex of the patient, activity of a drug, sensitivity to a drug, a time of administration, a pathway of administration, and an emission rate, duration of treatment, and simultaneously used drugs and other elements well-known in the medical field. The composition of the present disclosure may be administered as an individual therapeutic agent or administered in combination with other therapeutic agents, and sequentially or simultaneously administered with therapeutic agents in the related art. In addition, the composition of the present disclosure may be administered in single or multiple. It is important to administer an amount capable of obtaining a maximum effect with a minimal amount without side effects by considering the elements and it may be easily determined by those skilled in the art. A preferable dose of the composition of the present disclosure varies according to a condition and a weight of a patient, the degree of disease, a type of drug, a route and a period of administration, and a suitable total usage amount per day may be determined by a doctor within a correct medical judgment, but the composition may be administered with an amount of 0.001 to 1000 mg/kg, preferably 0.05 to 200 mg/kg, and more preferably 0.1 to 100 mg/kg one to several times per day. The subject is not particularly limited if the subject is a subject for preventing or treating the hair loss and any subject can be applied. For example, any subject such as non-human animals such as a monkey, a dog, a cat, a rabbit, a guinea pig, a rat, a mouse, a cow, a sheep, a pig, and a goat and the human may be applied, but is not limited thereto.

Meanwhile, the administration method of the pharmaceutical composition according to the present disclosure is not particularly limited, and the pharmaceutical composition may be parenterally, orally, or topically administered, and preferably parenterally administered. In the case of the parenteral administration, the pharmaceutical composition may be injected or infused intradermally, subcutaneously, intramuscularly, intravenously, intramedullary, intraarticularly, intra-synovially, intrathecally, intraspinally, preferably subcutaneously and transdermally, or administered in an applying form which is applied to a region of hair loss or applied to a region where the progress of hair loss is predicted. Further, the administration method is not particularly limited, and thus the pharmaceutical composition may be directly injected to the region where the progress of hair loss is predicted in an injection form. Further, the administration method is not particularly limited, and thus the pharmaceutical composition may be injected to artery, vein, or the like. The most preferable administration of the composition of the present disclosure may be performed through subcutaneous injection or skin application.

Further, the administration level selected from the composition follows activity of the active ingredient, a route of administration, severity of the hair loss to be treated, a condition of the hair loss to be treated, and a previous history. However, from an amount of the active ingredient lower than an amount required for achieving a desired therapeutic effect, until a desired effect is achieved, slowly increasing a dose is within the knowledge in the art and a preferable dose may be determined according to an age, a gender, a body type, and a weight. The composition may be additionally processed before being prepared as a pharmaceutically acceptable formulation and preferably, may be ground or polished into smaller particles. Further, the composition varies according to a condition of a patient and a patient to be treated.

The composition of the present disclosure may be a formulation which may be administered by a method of directly being applied or dispersed on a skin, for example, hair or scalp, for example, a formulation such as cream, lotion, ointment, aerosol, shampoo, gel, or pack. A method for a mixed ingredient or agent suitable for each formulation is known in the art. When these agents are prepare by those skilled in the art, various mixed ingredients used for preparing general external preparation may be properly selected and used.

The hair applied with the composition of the present disclosure includes all regions with hair roots and hair follicles throughout the body such as hair roots and hair follicles of the head, eyelashes and eyebrows, beards, armpits, and pubic hair.

Further, the present disclosure provides a pharmaceutical composition for preventing or treating hair loss, comprising a CXCL1 protein and minoxidil. Further, the present disclosure provides a pharmaceutical composition for promoting hair generation or hair growth, comprising a CXCL1 protein and minoxidil.

The minoxidil is a hair generation agent for preventing or treating hair loss and a drug that exhibits a hair generation effect by increasing the blood flow in the hair follicle a great effect. However, in the case of mixing the CXCL1 protein and the minoxidil of the present disclosure, a significantly excellent effect of preventing or treating the hair loss may be exhibited as compared with the effect of preventing or treating the hair loss which is verified in the case where the minoxidil is administered alone.

The CXCL1 protein and the minoxidil of the present disclosure may be mixed and used with a weight ratio of 1:1 to 1:20, respectively, preferably 1:1 to 1:15, and more preferably 1:1 to 1:10. In an exemplary embodiment of the present disclosure, a composition in which the CXCL1 protein and the minoxidil are mixed with 1 µg/ml and 10 µg/ml is provided.

Further, the present disclosure provides a quasi-drug composition for preventing or improving hair loss comprising a CXCL1 protein as an active ingredient. The quasi-drug composition may be a quasi-drug composition for preventing or improving hair loss further comprising minoxidil.

Further, the present disclosure provides a quasi-drug composition for promoting hair generation or hair growth, comprising a CXCL1 protein; or a CXCL1 protein and minoxidil as an active ingredient.

The term "quasi-drug product" in the present disclosure means an article except for a device, a machine, or an apparatus which is used for the purpose of diagnosing, treating, alleviating, handling or preventing a disease of a person or an animal and a product except for a device, a machine, or an apparatus which is used for the purpose of having a pharmacological effect on the structure or function of a person or animal, as an article corresponding to one of fibers, rubber products, or similar products thereof used for the purpose of treating, alleviating, handling or preventing diseases of human or animals, articles except for devices or machines and similar products with weakly acting on the human body or without acting directly on the human body, and formulations for sterilization, insecticidal and similar uses for the prevention of infection, and includes skin external and personal hygiene products.

In the case where the composition of the present disclosure is included in the quasi-drug for preventing or improving the hair loss or promoting hair generation or hair growth, the composition may be used as it is or may be used together with other quasi-drug ingredients and may be properly used according to a general method. A mixed amount of active ingredients may be suitably determined according to a use purpose.

The quasi-drug of the present disclosure is not particularly limited thereto, but may be prepared and used in a form of for example, creams, lotions, aerosols, shampoos, gels or packs.

In the case of the creams, lotions, aerosols, shampoos, gels or packs, base materials such as white petrolatum, yellow petrolatum, lanolin, bleached beeswax, cetanol, stearyl alcohol, stearic acid, hydrogenated oil, gelling hydrocarbon, polyethylene glycol, liquid paraffin, and squalane; solvents and dissolution aids such as oleic acid, myristic acid isopropyl, triisooctanoic acid glycerin, crotamiton, diethyl sebacate, diisopropyl adipate, hexyl laurate, fatty acid, fatty acid ester, aliphatic alcohol and vegetable oil; antioxidants such as tocopherol derivatives, L-ascorbic acid, dibutylhydroxytoluene, and butylhydroxyanisole; preservatives such as parahydroxybenzoic acid ester; humectants such as glycerin, propylene glycol and sodium hyaluronate; surfactants such as polyoxyethylene derivatives, glycerin fatty acid esters, sucrose fatty acid esters, sorbitan fatty acid esters, propylene glycol fatty acid esters, and lecithin; thickening agents such as carboxyvinyl polymer, xanthan gum, carboxymethylcellulose, carboxymethylcellulose sodium salts, hydroxypropylcellulose, hydroxypropylmethylcellulose, and the like are included.

In the case of an aerosol agent, base materials such as white petrolatum, yellow petrolatum, lanolin, bleached beeswax, cetanol, stearyl alcohol, stearic acid, hydrogenated oil, gelling hydrocarbon, polyethylene glycol, liquid paraffin, and squalane; solvents and dissolution aids such as oleic acid, myristic acid isopropyl, diisopropyl adipate, isopropyl sebacate, triisooctanoic acid glycerin, crotamiton, diethyl sebacate, hexyl laurate, fatty acid, fatty acid ester, aliphatic alcohol and vegetable oil; antioxidants such as tocopherol derivatives, L-ascorbic acid, dibutylhydroxytoluene, and butylhydroxyanisole; preservatives such as parahydroxybenzoic acid ester; humectants such as glycerin, propylene glycol and sodium hyaluronate; surfactants such as polyoxyethylene derivatives, glycerin fatty acid esters, sucrose fatty acid esters, sorbitan fatty acid esters, propylene glycol fatty acid esters, and lecithin; thickening agents such as carboxyvinyl polymer, xanthan gum, carboxymethylcellulose, carboxymethylcellulose sodium salts, hydroxypropylcellulose, hydroxypropylmethylcellulose, which are used in the preparation of ointments, creams, gels, suspensions, emulsions, solutions and lotions; additionally, various stabilizers, buffers, mating agents, suspensions, emulsifiers, fragrances, preservatives, subsolubilizers, and other suitable additives may be mixed.

Further, if necessary, stabilizers, preservatives, absorption promoters, pH adjusters, and other suitable additives may be mixed.

Further, the present disclosure provides a cosmetic composition for preventing or improving hair loss and a cosmetic composition for promoting hair generation or hair growth, comprising a CXCL1 protein; or a CXCL1 protein and minoxidil as an active ingredient.

The cosmetic composition may be a formulation of a hair tonic, a hair cream, a hair lotion, a hair shampoo, a hair rinse, a hair conditioner, a hair spray, a hair aerosol, pomade, a powder gel, a hair pack, a hair treatment, an eyebrow hair growth agent, an eyelash hair growth agent, and an eyelash nutrient as a skin quasi-drug formulation, but is not limited thereto.

Further, the composition for preventing or improving hair loss and promoting hair generation or hair growth of the present disclosure may be used for pets by changing the formulation. For example, like a pet shampoo and a pet rinse, the composition may be prepared in various forms such as solution, sol gel, emulsion, oil, wax, aerosol, and prepared by adding a neutral detergent with less irritation to the pet skin and excellent moisture retention.

Further, the cosmetic composition of the present disclosure may include generally acceptable ingredients in addition to the active ingredient without limitation and for example, may include general additives such as antioxidants, stabilizers, solubilizers, vitamins, pigments and flavors, and carriers.

In the case of the shampoo, any one or more of a synthetic surfactant which is a cleaning ingredient, a preservative, a thickener, a viscosity regulator, a pH adjusting agent, a perfume, a dye, a hair conditioning agent, and water may be included. A synthetic anionic surfactant of the synthetic surfactants is alkyl and alkyl ether sulfates, and as a representative example, sodium lauryl sulfate, ammonium lauryl sulfate, triethanolamine lauryl sulfate, sodium polyoxyethylene lauryl sulfate, ammonium polyoxyethylene lauryl sulfate, or the like is included. Further, a synthetic amphoteric surfactant of the synthetic surfactants is alkyl betamine and alkylamidopropyl betaine, and as a representative example, cocodimethyl carboxymethyl betaine, lauryl dimethyl carboxymethyl betaine, lauryl dimethyl alpha-carboxyethyl betaine, cetyl dimethyl carboxymethyl betaine, cocamidopropyl betaine, or the like is included. The nonionic surfactant is alkanolamide and amine oxide, and lauryl diethylamine oxide, coconut oil alkyldimethylamine oxide, lauric acid diethanolamide, palm oil fatty acid diethanolamide, palm oil fatty acid monoethanolamide, or the like is included.

Any ingredient used in the present disclosure is widely known to the expert in the art as any general ingredient for maintaining basic property and quality as the shampoo. As any ingredient, a pearlescent adjuvant, a preservative, a thickener and a viscosity adjusting agent, a pH adjusting agent, a perfume, a dye, and a hair conditioning agent are included. For example, a pearlescent adjuvant such as ethylene glycol monostearate, and ethylene glycol distearate; a preservative such as methyl ρ-Hydroxybenzoate and a mixture of methyl chloroisothiazolinone and methyl isothiazolinone; a thickener and a viscosity adjusting agent such as sodium chloride, ammonium chloride, and propylene glycol; a pH adjusting agent such as citric acid, phosphoric acid, sodium hydroxide, and potassium hydroxide; a hair conditioning agents such as polyquaternium-10, polyquaternium-7, methylpolysiloxane, dimethicone copolyol, and hydrolyzed animal protein, and a dye such as water-soluble tar are used, and further, a perfume may be used.

Further, the present disclosure provides a food composition for preventing or improving hair loss and a food composition for promoting hair generation or hair growth comprising a CXCL1 protein; or a CXCL1 protein and minoxidil as an active ingredient.

The food composition of the present disclosure may be a health functional food, and the "health functional food" means a food manufactured or processed by using raw materials or ingredients having useful functions to the human body in accordance with the Health Functional Food Act, No. 6727, and the "functionality" means intake for adjusting nutrients on a structure and a function of the human body or obtaining a useful effect for health such as a physiological action.

The food composition may additionally include food additives, and suitability as the "food additives" is determined based on a scale and a standard for the corresponding item according to the general regulations and general test methods of the Food Additives Codex approved by the Korean Food and Drug Administration unless otherwise provided.

Items disclosed in the "Food Additives Codex" may include, for example, chemical compounds such as ketones, glycine, potassium citrate, nicotinic acid, and cinnamic acid, natural additives such as persimmon extract, licorice extract, crystalline celluloses, and guar gums, and mixed agents such as a sodium L-glutamate agent, a noodles-added alkaline agent, a preservative agent, or a tar coloring agent.

The foods including the active ingredient of the present disclosure may include confectionery such as bread, rice cake, nuts, candy, chocolate, chewing gum, and jam; ice cream products such as ice cream, frozen desserts, and ice cream powder; dairy products such as milk, low fat milk, lactase milk, processed milk, goat milk, fermented milk, butter milk, concentrated milk, milk cream, butter milk, natural cheese, processed cheese, milk powder, and milk serums; meat products such as meat products, egg products, and hamburgers; fish products such as fish processed products such as fish paste, ham, sausage, and bacon; noodles such as ramen noodles, dried noodles, fresh noodles, instant fried noodles, instant dried noodles, improved noodles, frozen noodles, and pastas; beverages such as fruit drinks, vegetable beverages, carbonated beverages, soybean milks, lactic beverages such as yogurt, and mixed drinks; seasonal foods such as soy sauce, miso, Kochujang, Chunjang, Chonggukjang, Mixed Jang, vinegar, sauces, tomato ketchup, curry, and dressing; margarine, shortening and pizza, but are not limited thereto.

The composition of the present disclosure may additionally include various nutrients, vitamins, electrolytes, flavoring agents, coloring agents, pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, or the like in addition to the ingredients. Besides, the composition of the present disclosure may include pulps for preparing natural fruit juices, fruit juice beverages, and vegetable beverages. The ingredients may be used independently or in combination. Although the ratio of the additives does not matter, generally, the ratio is selected in a range of 0.01 to 0.1 part by weight per 100 parts by weight of the composition of the present disclosure.

In the beverage composition including the active ingredient of the present disclosure, other ingredients are not particularly limited except for including the protein, and like a general beverage, various flavoring agents or natural carbohydrates, or the like may be included as an additional ingredient. Examples of natural carbohydrates include general sugars such as monosaccharides (for example, glucose, fructose, and the like); disaccharides (for example, maltose, sucrose, and the like); and polysaccharides (for example, dextrin, cyclodextrin, and the like), and sugar alcohols such as xylitol, sorbitol, and erythritol. As the flavoring agents other than the above examples, natural flavoring agents (thaumatin, stevia extract (for example, Rebaudioside A, Glycyrrhizin, and the like) and synthetic flavoring agents (saccharin, aspartame, and the like) may be advantageously used.

Further, the present disclosure provides a complex formulation for preventing or treating hair loss comprising a CXCL1 (chemokine (C-X-C motif) ligand 1) protein and minoxidil.

The complex formulation includes the CXCL1 (chemokine (C-X-C motif) ligand 1) protein and the minoxidil as an active ingredient, and the CXCL1 protein and the minoxidil may be included with a weight ratio of 1:1 to 1:20, respectively, preferably 1:1 to 1:15, and more preferably 1:1 to 1:10. In an exemplary embodiment of the present disclosure, a composition in which the CXCL1 protein and the minoxidil are mixed with 1 μg/ml and 10 μg/ml is provided.

The complex formulation may generate new hair about three times greater than that of a PBS-administered group to exhibit an excellent effect of promoting hair generation. The effect is a significantly excellent effect as compared with the minoxidil-alone administration and a significantly excellent effect as compared with the CXCL1 protein-alone administration which generates new hair which is about two times greater than that of the PBS-administered group. It can be seen that the complex formulation exhibits a synergic effect of promoting hair generation and promoting hair growth.

Further, the present disclosure provides a method for preventing or treating hair loss comprising treating with a CXCL1 protein; or a CXCL1 protein and minoxidil to a subject.

Further, the present disclosure provides a method for improving hair loss comprising treating with a CXCL1 protein; or a CXCL1 protein and minoxidil to a subject.

Another object of the present disclosure provides a method for promoting hair generation or hair growth comprising treating with a CXCL1 protein; or a CXCL1 protein and minoxidil to a subject.

The term "preventing" used in this specification means all activities which suppress or delay hair loss by administering the composition of the present disclosure and the "improving" or "treating" means all activities which improve or beneficially change symptoms associated with hair loss by the composition of the present disclosure.

The term "subject" used in this specification is a subject in which hair loss is in progress or may be in progress and a subject requiring an effect of hair generation and hair growth, and means a subject in which hair loss is delayed, suppressed, or improved or hair generation or hair growth may be promoted by treating with the CXCL1 protein; or the CXCL1 protein and the minoxidil of the present disclosure. The subject may be mammals including the human.

The term "treatment" used in this specification may include all activities which administer and contact the CXCL1 protein; or the CXCL1 protein and the minoxidil to the subject without limitation.

Hereinafter, the present disclosure will be described in more detail by Examples and Test Examples. However, the following Examples and Test Examples are exemplified to more easily understand the present disclosure and the contents of the present disclosure is not limited by Examples, and in this case, used technical terms and scientific terms are generally understood by those skilled in the art if there is no other definition.

Example 1. Obtainment of CXCL1 and Minoxidil

A chemokine (C-X-C motif) ligand 1 (CXCL1) protein was purchased from Peprotech. A result of analyzing an amino acid sequence and a DNA base sequence of the obtained CXCL1 protein was illustrated in SEQ ID NO:1 and SEQ ID NO:2.

Minoxidil was used by purchasing 2% (w/v) minoxidil which was sold under the trade name of Rogaine® from Jonhson & Johnson Healthcare Co., Ltd. in USA.

Example 2. Verification of Cell Proliferation Effect of CXCL1

A human dermal papilla cell (DPC) proliferation test which is a representative in vitro cell test system for measuring hair proliferation was performed. 1 ng/ml or 5 ng/ml of the CXCL1 protein in Example 1 was treated to DPC, proliferation for 40 hrs was measured, and the result was illustrated in FIG. 1.

As illustrated in FIG. 1, it was verified that when the CXCL1 protein was treated to DPC, cell proliferation was increased compared to cells without treating with the CXCL1 protein.

From the result, it was verified that the CXCL1 protein had an excellent cell proliferation effect to be used for treating hair loss or promoting hair growth.

Example 3. Verification of Hair Generation Effect of CXCL1

For a test for verifying a hair generation effect, the back of a 7-week-old C3H/HeN mouse was stabilized by removing hair by using a hair removal agent. After one day, 100 ng/ml of a human chemokine (C-X-C motif) ligand 1 (CXCL1) (SEQ ID NO:1) protein was subcutaneously injected to the back once. As a control, phosphate buffered saline (PBS) including 0.1% BSA at the same volume lysed with the CXCL1 protein was subcutaneously injected. Thereafter, the hair generation of the back of the hair-removed mouse was traced and observed for 15 days. A photograph of tracing and observing the back of the mouse with hair generation was illustrated in FIG. 2.

As illustrated in FIG. 2, it was verified that the hair generation was more excellent in the group treated with the CXCL1 protein compared with the control.

Further, after 15 days, the hair of the back of the mouse with newly hair generation was removed by using a knife and then the result of measuring the weight of the obtained hair was illustrated in FIG. 3.

As illustrated in FIG. 3, in the control, the measured hair weight was 40 mg, whereas the group treated with the CXCL1 protein was 80 mg, and as a result, it was verified that in the case of the group treated with the CXCL1 protein, an effect of promoting the hair generation was excellent.

Example 4. Verification of Hair Generation Effect of CXCL1 Protein and Minoxidil Complex From the result, it was verified that the CXCL1 protein ingredient had an excellent hair generation effect. In addition, in the case of combining and using the minoxidil and the CXCL1 protein which were commercialized as a hair generation agent, an experiment for verifying whether the hair generation effect may be better was performed. First, for an experiment for hair regeneration, long hair of a 7-week-old C3H/HeN mouse and the like was shortly cut by using a hair cutting machine and thereafter, the hair was completely removed by using a hair removal agent. After the hair-removed mouse was stabilized for one day, a recombinant protein CXCL1 was mixed with 2% minoxidil (Women's Rogaine, Johnson & Johnson Healthcare Products, USA) to be 1 µg/ml and 10 µg/ml, respectively. The mixture of the minoxidil and the CXCL1 protein was applied to the back skin of the hair-removed mouse for 14 days by 100 µg/ml per day. As a control, a PBS-alone applied group and a 2% minoxidil-alone treated group were set. The hair generation in the back of the mouse was tracked and observed for 14 days and newly generated hair was obtained again and the weight was measured, and the result was illustrated in FIGS. 4 and 5.

As illustrated in FIG. 4, in the case of the PBS-alone and minoxidil-alone treated groups, even after 14 days, in some mice, there was no hair generation effect and the new hair was not verified in the entire back, but in the group of mixing and applying the minoxidil and the CXCL1 protein, it was verified that the effective hair generation effect was exhibited in the backs of all of the mice.

Further, as illustrated in FIG. 5, as the result of quantitatively analyzing an amount of newly generated hair, in the PBS-alone treated group, 20 mg of hair was obtained and in the minoxidil-alone treated group, about 30 mg of hair was obtained. However, in the mixture administered group of the present disclosure, it was verified that 60 mg or more of hair was obtained which was three times greater than that of the PBS-alone treated group and two times greater than the minoxidil-alone treated group. Such a result indicates that the CXCL1 protein of the present disclosure has an effect of promoting hair generation at the time of administering alone and may induce a significantly excellent effect of promoting hair generation as compared with an effect of promoting hair generation of minoxidil at the time of administering with the minoxidil.

Hereinafter, Preparation Examples of the pharmaceutical composition for preventing or treating hair loss and the cosmetic composition and food composition for preventing or improving the hair loss and promoting or stimulating hair generation or hair growth comprising the active ingredient of the present disclosure will be described, but the present disclosure is not limited thereto, but will be just described in detail.

Preparation Example 1. Preparation of Pharmaceutical Formulation

1. Preparation of Powder

| | |
|---|---|
| CXCL1 protein; or CXCL1 protein and minoxidil | 20 mg |
| Lactose | 100 mg |
| Talc | 10 mg |

The ingredients were mixed and packed in an airtight bag to prepare the powder.

2. Preparation of Tablet

| | |
|---|---|
| CXCL1 protein; or CXCL1 protein and minoxidil | 10 mg |
| Corn starch | 100 mg |
| Lactose | 100 mg |
| Magnesium stearate | 2 mg |

The ingredients were mixed and tableted according to a general tablet preparing method to prepare the tablet.

3. Preparation of Capsule

| | |
|---|---|
| CXCL1 protein; or CXCL1 protein and minoxidil | 10 mg |
| Crystalline cellulose | 3 mg |
| Lactose | 14.8 mg |
| Magnesium stearate | 0.2 mg |

The ingredients were mixed and filled in a gelatin capsule according to a general capsule preparing method to prepare the capsule.

4. Preparation of Injection

| | |
|---|---|
| CXCL1 protein; or CXCL1 protein and minoxidil | 10 mg |
| Mannitol | 180 mg |
| Sterile distilled water for injection | 2974 mg |
| $Na_2HPO_4 2H_2O$ | 26 mg |

The injection was prepared with the content of ingredients per ampoule (2 ml) according to a general preparing method of the injection.

5. Preparation of Liquid Solution

| | |
|---|---|
| CXCL1 protein; or CXCL1 protein and minoxidil | 20 mg |
| Isomerized glucose | 10 g |
| Mannitol | 5 g |
| Purified water suitable amount | |

According to a general preparing method of the liquid solution, respective ingredients were added in purified water and dissolved, added with a suitable amount of lemon flavoring, and mixed and then added with purified water so as to be adjusted to the entire 100 ml, and then filled in a dark amber bottle and sterilized to prepare the liquid solution.

Preparation Example 2. Preparation of Cosmetic Formulation

1. Preparation of Hair Lotion

| | |
|---|---|
| CXCL1 protein; or CXCL1 protein and minoxidil | 0.6 wt % |
| Glycerin | 5.1 wt % |
| Propylene glycol | 4.2 wt % |
| Tocopheryl acetate | 3.0 wt % |
| Liquid paraffin | 4.6 wt % |
| Triethanolamine | 1.0 wt % |
| Squalane | 3.1 wt % |
| Macadamia nut oil | 2.5 wt % |
| Polysorbate 60 | 1.6 wt % |
| Sorbitan Sesquioleate | 1.6 wt % |
| Propylparaben | 0.6 wt % |
| Carboxyl vinyl polymer | 1.5 wt % |
| Fragrance | trace |
| Antiseptic agent | trace |
| Purified water | remaining amount |

2. Preparation of Hair Cream

| | |
|---|---|
| CXCL1 protein; or CXCL1 protein and minoxidil | 1.0 wt % |
| Glycerin | 4.0 wt % |
| Vaseline | 3.5 wt % |
| Triethanolamine | 2.1 wt % |
| Liquid paraffin | 53 wt % |
| Squalane | 3.0 wt % |
| Wax | 2.6 wt % |
| Tocopheryl acetate | 5.4 wt % |
| Polysorbate 60 | 3.2 wt % |
| Carboxyl vinyl polymer | 1.0 wt % |
| Sorbitan Sesquioleate | 3.1 wt % |
| Fragrance | trace |
| Antiseptic agent | trace |
| Purified water | remaining amount |

3. Preparation of Hair Shampoo

| | |
|---|---|
| CXCL1 protein; or CXCL1 protein and minoxidil | 5.8 wt % |
| Sodium lauryl sulfate | 35 wt % |
| Glycerin | 1 wt % |
| Lauramide DEA | 3.5 wt % |
| Propylene glycol | 1 wt % |
| Cocamidopropyl betaine | 1 wt % |
| Cetyl alcohol | 0.1 wt % |
| Glycol distearate | 0.5 wt % |
| Butylene glycol | 8 wt % |
| Methylparaben | 0.2 wt % |
| Triethanolamine | 0.1 wt % |
| Citric acid | 0.1 wt % |
| Polyquaternium-7 | 0.2 wt % |
| Polyquaternium-10 | 0.12 wt % |
| Olive oil fiji-7 ester | 0.2 wt % |
| Fragrance | trace |
| Antiseptic agent | trace |
| Purified water | remaining amount |

Preparation Example 3. Preparation of Food Formulation

1. Preparation of Health Food

| | |
|---|---|
| CXCL1 protein; or CXCL1 protein and minoxidil | 100 mg |
| Vitamin mixture | suitable amount |
| Vitamin A acetate | 70 g |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 g |
| Vitamin C | 10 mg |
| Biotin | 10 g |
| Nicotinamide | 1.7 mg |
| Folic acid | 50 g |
| Calcium pantothenate | 0.5 mg |
| Mineral mixture | suitable amount |
| Ferrous sulfate | 1.75 mg |
| Zinc oxide | 0.82 mg |
| Magnesium carbonate | 25.3 mg |
| First potassium phosphate | 15 mg |
| Second potassium phosphate | 55 mg |
| Potassium citrate | 90 mg |
| Calcium carbonate | 100 mg |
| Magnesium chloride | 24.8 mg |

A composition ratio of the mixture of vitamins and mineral was set by mixing ingredients relatively suitable for a health food, but a mixed ratio may be randomly modified. According to a general preparing method of the health food, the ingredients were mixed to prepare granules and may be used for preparing the health food composition according to a general method.

2. Preparation of Health Beverage

| | |
|---|---|
| CXCL1 protein; or CXCL1 protein and minoxidil | 100 mg |
| Vitamin C | 15 g |
| Vitamin E (powder) | 100 g |
| Iron lactate | 19.75 g |
| Zinc oxide | 3.5 g |
| Nicotinamide | 3.5 g |
| Vitamin A | 0.2 g |
| Vitamin B1 | 0.25 g |
| Vitamin B2 | 0.3 g |
| Water | required amount |

According to a general method of preparing health beverages, the ingredients were mixed, stirred and heated for about 1 hour at 85° C., a prepared solution was filtrated to be obtained in a sterilized container of 2 L, sterilized after sealing, and refrigerated, and then used for preparing the health beverage composition of the present disclosure.

The composition ratio was set by mixing ingredients relatively suitable for a favorite beverage, but a mixed ratio may be randomly modified and implemented according to regional and national preference such as demand layers, demand countries, and a purpose of use.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for treating or reducing hair loss, or promoting hair generation or hair growth comprising administering to a subject a composition comprising a chemokine (C-X-C motif) ligand 1 (CXCL1) protein; or a CXCL1 protein and minoxidil as active ingredient, wherein the CXCL1 protein has the amino acid sequence represented by SEQ ID NO:1.

2. The method of claim 1, wherein the hair loss is one or more kind selected from the group consisting of male pattern hair loss, female pattern hair loss, round hair loss and resting hair loss.

3. The method of claim 1, wherein the administration is parenterally, orally, or topically.

4. The method of claim 3, wherein the administration is parenterally.

5. The method of claim 1, wherein the CXCL1 protein and the minoxidil has a weight ratio of 1:1 to 1:20, respectively.

6. The method of claim 1, which is in a pharmaceutical formulation, a quasi-drug formulation, cosmetic formulation, or food formulation.

* * * * *

SEQUENCE LISTING

<160> NUMBER OF SEQ ID NOS: 2

<210> SEQ ID NO 1
<211> LENGTH: 107
<212> TYPE: PRT
<213> ORGANISM: Artificial Sequence
<220> FEATURE:
<223> OTHER INFORMATION: CXCL1 protein

<400> SEQUENCE: 1

Met Ala Arg Ala Ala Leu Ser Ala Ala Pro Ser Asn Pro Arg Leu Leu
 1               5                  10                  15

Arg Val Ala Leu Leu Leu Leu Leu Val Ala Ala Gly Arg Arg Ala
                20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
        50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 2
<211> LENGTH: 324
<212> TYPE: DNA
<213> ORGANISM: Artificial Sequence
<220> FEATURE:
<223> OTHER INFORMATION: CXCL1 DNA Sequence

<400> SEQUENCE: 2
atggcccgcg ctgctctctc cgccgccccc agcaatcccc ggctcctgcg agtggcactg      60
ctgctcctgc tcctggtagc cgctggccgg cgcgcagcag gagcgtccgt ggccactgaa     120
ctgcgctgcc agtgcttgca gaccctgcag ggaattcacc ccaagaacat ccaaagtgtg     180
aacgtgaagt cccccggacc ccactgcgcc caaaccgaag tcatagccac actcaagaat     240
gggcggaaag cttgcctcaa tcctgcatcc cccatagtta agaaaatcat cgaaaagatg     300
ctgaacagtg acaaatccaa ctga                                            324